United States Patent [19]

DeGraw et al.

[11] Patent Number: 4,746,659

[45] Date of Patent: * May 24, 1988

[54] DIASTEREOMERS OF 10-ALKYL-10-DEAZAMINOPTERINS AND PROCESS FOR PREPARING THE SAME

[75] Inventors: Joseph I. DeGraw; Pamela H. Christie, both of Sunnyvale, Calif.: Francis M. Sirotnak, New York, N.Y.

[73] Assignees: SRI International, Menlo Park, Calif.; Sloan Kettering Institute for Cancer Research, New York, N.Y.

[*] Notice: The portion of the term of this patent subsequent to Jan. 18, 2000 has been disclaimed.

[21] Appl. No.: 814,720

[22] Filed: Dec. 30, 1985

[51] Int. Cl.[4] .................. A61K 31/505; C07D 475/08
[52] U.S. Cl. ..................................... 514/249; 514/258; 544/260

[58] Field of Search ............... 544/258, 260; 514/249, 514/258

[56] References Cited

U.S. PATENT DOCUMENTS 4,369,319  1/1983  DeGraw, Jr. et al. ............. 544/260
4,393,064  7/1983  DeGraw, Jr. et al. ............. 514/249

*Primary Examiner*—Donald G. Daus
*Assistant Examiner*—Mark W. Noel

[57] ABSTRACT

Diastereomers of 10-alkyl-10-deazaminopterins are provided, as well as a synthesis for their preparation as the individual d,L. and l,L.-diastereomers, the d,L-10-ethyl diastereomer being three times as potent against L1210 cells as the l,L-10-ethyl diastereomer, and the l,L-10-ethyl diastereomer being approximately one-half as toxic as the d,L-10-ethyl diastereomer.

47 Claims, No Drawings

DIASTEREOMERS OF 10-ALKYL-10-DEAZAMINOPTERINS AND PROCESS FOR PREPARING THE SAME

ORIGIN OF INVENTION

The invention described herein was in part made in the course of work under a grant or award from the National Institute of Health, Department of Health, Education and Welfare.

In the *Journal of Medicinal Chemistry* 17 552 (1974), DeGraw, Kisliuk, Gaumont, Baugh and Nair reported on the synthesis and antifolate activity of 10-deazaminopterin. The antimicrobial and antitumor activities of the powerful dihydrofolic reductase inhibitors aminopterin and its N-10 methyl derivative, methotrexate, are well known, and numerous analogues have been made to further improve the potency, cell penetration and toxicity properties of these compounds. As part of a continuing program to investigate structure-activity relationships in folic acid analogues, DeGraw et al were interested in the effects of replacement of the nitrogen atom in the side chain of aminopterin, and reported on the synthesis and biological activity of 10-deazaminopterin in this paper.

Continuing work with 10-deazaminopterin led to the discovery of its antileukemic activity, and efficacy in treating various ascites tumor systems.

Leukemia is an actue or chronic disease of unknown cause in man and other warm-blooded animals. It is characterized by an abnormal increase in the number of immature leukocytes in the tissues of the body and in the circulating blood. The disease apparently affects the blood-forming organs, and is classified according to the type of leukocyte that is being proliferated abnormally. The disease is one of a number of forms of neoplastic disease, and the development of drugs for amelioration or curing the disease has occupied the attention of research organizations for many years, and until most recently without appreciable success. Today, many forms of leukemia can be effectively treated with drugs. In the case of combination chemotherapy with acute lymphocytic leukemia in children a large percentage (50–60%) of five year survivals are obtained, and the disease is now classified as curable.

DeGraw and Sirotnak, U.S. Pat. No. 4,393,064, patented July 12, 1983 disclosed that leukemia, as well as other malignancies, including ascitic tumors, can be ameliorated in warm-blooded lower animals by the administration of 10-deazaminopterin, a nontrivial analogue of methotrexate, one of the current drugs of choice for the treatment of leukemia in the clinic.

10-deazaminopterin has the structure:

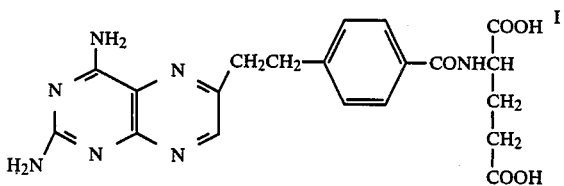

The relationship between N-deazaminopterin and the N-10 methyl derivative of aminopterin, methotrexate, is apparent from the following:

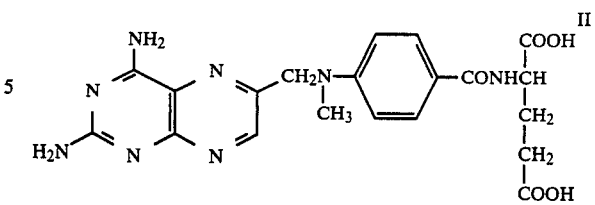

4-Amino-4-deoxy-10-deazapteroic acid, a key intermediate for synthesis of 10-deazaminopterin, was first prepared by DeGraw, Brown, Kisliuk and Gaumont, *Journal of Medicinal Chemistry* 14 866 (1971). DeGraw, Tsakotellis, Kisliuk, and Gaumont, *Journal of Heterocyclic Chemistry* 8 105 (1971) had reported the potent growth-inhibitory activity of 10-deazapteroic acid and its tetrahydro derivative against *Streptococcus faecium*, a folate-dependent organism. Activity was greatly enhanced by reduction to the tetrahydro compound. Accordingly, it was thought that the 2,4-diamino-pteridines should be investigated, because they would be expected to be more capable of cell penetration, and among the 2,4-diamino-pteridines prepared was 4-amino-4-deoxy-10-deazapteroic acid, the compound shown under the Scheme I, Series d, at page 367 of the article.

DeGraw and Sirotnak, U.S. Pat. Nos. 4,369,319, patented Jan. 18, 1983 and 4,433,147, patented Feb. 21, 1984, in further work based on 10-alkyl derivatives of 10-deazaminopterin, disclosed that leukemia, as well as other malignancies, including ascitic tumors, can be ameliorated in warm-blooded lower animals by the administration of 10-alkyl derivatives of 10-deazaminopterin.

10-alkyl-10-deazaminopterin compounds have the structure:

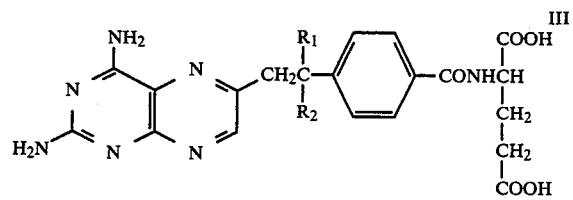

In the compound 10-deazaminopterin, $R_1$ and $R_2$ are both hydrogen. In the alkyl derivatives, either or both of $R_1$ and $R_2$ can be alkyl having from one to about eight, preferably one or two carbon atoms. When only one of $R_1$ and $R_2$ is alkyl, the other is hydrogen.

Exemplary $R_1$ and $R_2$ alkyl include methyl, ethyl, propyl, isopropyl, butyl, isobutyl, sec-butyl, terty-butyl, amyl, iso-amyl, sec-amyl, tert-amyl, hexyl, iso-hexyl, heptyl, iso-heptyl, octyl, iso-octyl, 2-ethyl hexyl and tert-octyl.

DeGraw, Brown, Tagawa, Kisliuk, Gaumont and Sirotnak, *Journal of Medicinal Chemistry* 25 1227 (1982), reported the synthesis of 10-methyl and 10-ethyl-10-deazaminopterin and in vitro observation on their activity against bacterial and L1210 cells, and antileukemic activity in L1210-bearing mice. The 10-ethyl compound has been found to be considerably more effective than methotrexate or 10-deazaminopterin in a number of experimental murine tumor models. (Sirotnak, DeGraw, Chello, Moccio and Dorick, *Cancer Treat. Rep.* 66 351 (1982), Sirotnak, DeGraw, Moccio, Samuels and Gautas, *Cancer Chemother. Pharmacol.* 12 18 (1984) and Sirotnak, DeGraw, Schmid, Goutas and Moccio, *Cancer Chemother. Pharmacol.* 12 26 (1984)). More recently, 10-ethyl-10-deazaminopterin has been shown to cause frank regressions in human mammary, lung and colon tumor xenografts in nude mice. (Schmid, Sirotnak, Otter and DeGraw, *Cancer Treat. Rep.* 69 551 (1985)). Clinical trials have in fact been initiated (Wertheim, Kris, Gralla, O'Connell, Kinahan, Cibas, Williams, Bauer, Farag, Fanucchi, and Young, 76th Meeting, *Amer. Assoc. Cancer Research*, Houston, Tex., May 22–25, 1985, paper 704) for 10-ethyl-10-deazaminopterin, whose primary advantage appears to lie in its enhanced differential penetration into tumors, as opposed to normal tissue. (Sirotnak and DeGraw, *Folate Antagonists as Therapeutic Agents* (F. M. Sirotnak, ed.) New York, Academic Press, Vol. 2, pp. 43–91 (1984)). This enhanced transport takes place at an active-transport protein in the cell wall, and represents one of the few examples whereby an antitumor drug takes advantage of a fundamental difference in proteinaceous materials between tumor and normal cells. A secondary advantage is the enhanced polyglutamation of the compound after it enters the cell. The polyglutamyl species retains inhibitory potency, but has diminished efflux from the cell.

As is apparent from the above structure, the asymmetric 10-alkyl-10-deazaminopterin molecule of Formula III in which $R_1$ and $R_2$ at the 10-position are different has two chiral centers, one at the 10-position, and one at the alpha carbon of the glutamate moiety. When using the L-isomers obtained by incorporation of L-glutamate, the synthesis shown at columns 2 and 4 of U.S. Pat. Nos. 4,369,319 and 4,433,147 affords compounds which are completely racemic about the 10-position.

The diastereomeric mixtures of U.S. Pat. Nos. 4,369,319 and 4,443,147 thus lack resolution at the 10-position and accordingly can be designated as racemic mixtures.

In accordance with this invention, a new synthesis is provided that affords the d,L isomers and the l,L isomers of 10-alkyl-10-deazaminopterins of Formula III as the individual diastereoisomers.

Further in accordance with the invention, the d,L and l,L isomers of 10-alkyl-10-deazaminopterins of Formula III are provided as new compounds, with distinctive and valuable properties.

The d,L isomer of 10-ethyl-10-deazaminopterin, for example, is significantly more effective in the inhibition of dihydrofolate reductase derived from L1210 cells, and in inhibition of growth for L1210 cells. The d,L isomer of 10-ethyl-10-deazaminopterin, for example, also displays an approximately three-fold greater potency against *L. casei* enzyme.

The l,L isomer of 10-ethyl-10-deazaminopterin, for example, on the other hand, in evaluation in vivo against L1210 leukemia in mice, displays a toxicity that is about one-half that of the d,L isomer. The lower toxicity is important, since it indicates that a higher dosage of the l,L-isomer can be administered in clinical applications.

Accordingly, the l,L isomer of 10-ethyl-10-deazaminopterin, for example, is expected to have utility in the treatment of human cancer. Furthermore, by analogy to methotrexate, the d,L isomer as well as the l,L isomer of 10-ethyl-10-deazaminopterin, for example, should have utility in the treatment of rheumatoid arthritis, since they are expected to be immune suppressants to a similar degree of methotrexate. The much lower toxicity of the l,L isomer should confer a significant advantage, in the treatment of arthritis on a chronic treatment basis. It further appears that other 10-alkyl diastereomers should be analogous to the 10-dethyl diastereomers in this property.

The invention accordingly also provides a process of treating leukemia and ascitic tumors, and ameliorating rheumatoid arthritis, which comprises administering to a warm-blooded animal having an abnormal proportion of leukocytes or other evidences of the malignancy, or rheumatoid arthritis, a therapeutic nontoxic amount of d,L or l,L-10-ethyl- and other 10-alkyl-10-deazaminopterins, as such or in the form of a pharmaceutically acceptable salt thereof. These salts are formed with one or more free $NH_2$ groups of the 10-alkyl-10-deazaminopterin.

The process of the invention for the preparation of d,L-10-alkyl-10-deazaminopterin and l,L-10-alkyl-10-deazaminopterin is a synthesis in which the d,L or l,L-4-amino-4-desoxy-10-ethylpteroic acid is coupled with diethyl L-glutamate, to yield the d,L or l,L diastereomer. Resolution of the racemic precursors is accomplished at the intermediate 3-p-carbomethoxyphenylalkanoic acid. The following are the steps of the reaction synthesis, exemplified by $R_1$ as ethyl $C_2H_5$ and $R_2$ as hydrogen.

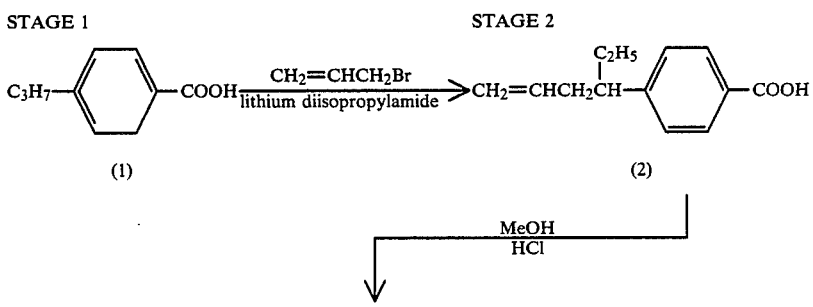

-continued
STAGE 3
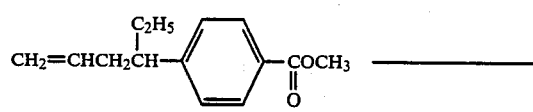
(3)
STAGE 4
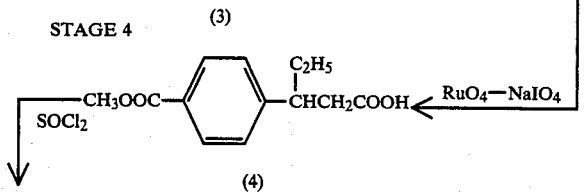
(4)
STAGE 5
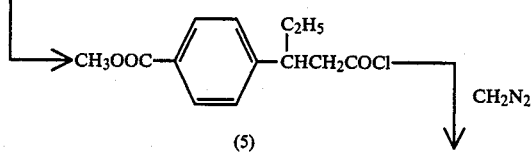
(5)
STAGE 6
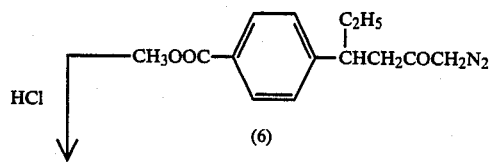
(6)
STAGE 7
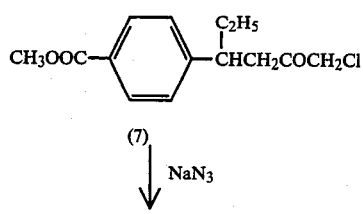
(7)
STAGE 8                    STAGE 9
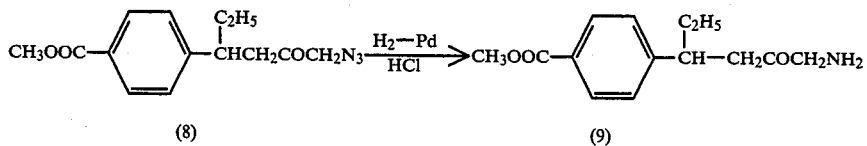
(8)                        (9)
STAGE 10
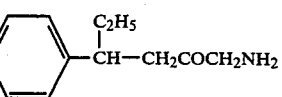
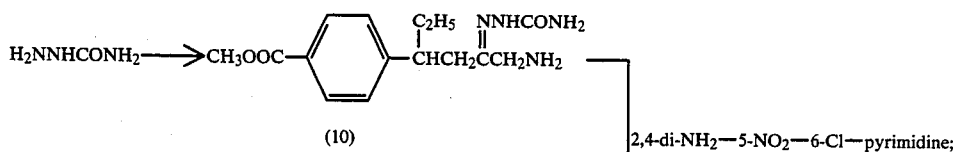
(10)
2,4-di-NH$_2$—5-NO$_2$—6-Cl—pyrimidine;
90% CF$_3$COOH
STAGE 11
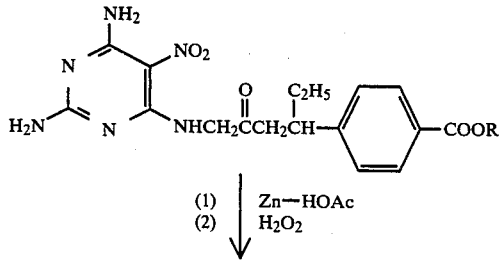
(1) | Zn—HOAc
(2) | H$_2$O$_2$

STAGE 12

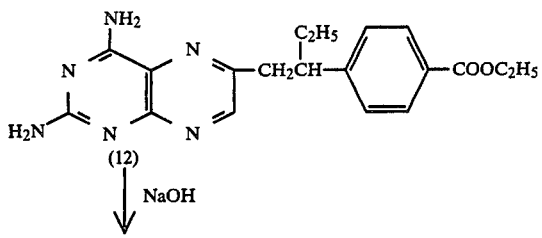

STAGE 13

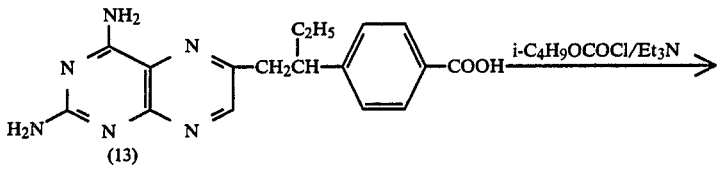

STAGE 14

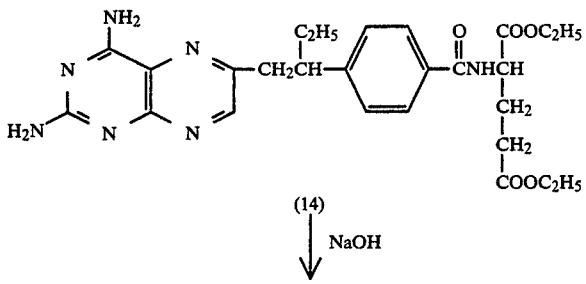

STAGE 15

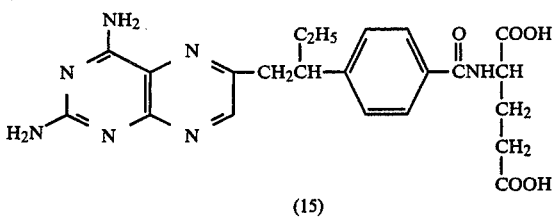

As the synthesis scheme shows, alkylation of the dianion of p-propylbenzoic acid (1) with allyl bromide, followed by esterification of the acid (2) with methanol, yields 4-p-carbomethoxyphenyl-1 hexene (3). Oxidation of the olefinic group with $NaIO_4$ in aqueous acetone, as catalyzed by $RuO_4$, results in degradation of the terminal carbon, to afford 3-p-carbomethoxyphenylvaleric acid (4). Recrystallization of the salt with d-α-methylbenzylamine leads to the d-form of (4) $[\alpha]+22.7°$, while similar treatment of the 1-α-methylbenzylamine salt gives the l-form of (4) $[\alpha]-24.1°$.

The racemic acids (4) and their resolved d,L and l,L forms are then carried separately through the sequence shown, to yield the target d,L or l,L diastereomer (15). This process begins with conversion of the acid chloride (5) of (4) to the chloromethyl ketone (7) via the diazomethyl ketone (6) intermediate. Displacement of the chloride with sodium azide in 80% MeOH affords the azidomethyl ketone (8). Hydrogenation of the azide over Pd black in the presence of HCl gives the amino ketone (9), which is isolated and characterized as the crystalline picrate salt. The ketone picrate (9) is directly converted to the semicarbazone derivative (10) by treatment with semicarbazide hydrochloride in 70% EtOH. Exchange of picrate salt for hydrochloride is easily accomplished in quantitative yield by stirring with Dowex 2($Cl^-$) resin in aqueous EtOH.

Alkylation of the free bases of (10) with 2,4-diamino-5-nitro-6-chloropyrimidine, in the presence of an equivalent of 2,4,6- or symmetrical collidine, abbreviated as s-collidine, followed by hydrolysis of the intermediate semicarbazones in 90% $CF_3COOH$, affords the 2,4-diamino-6-pyrimidinylamino ketone (11). Reduction of the nitro group with zinc dust in acetic acid causes ring closure to the dihydro pteridine which is oxidized in situ to the diamino pteridine ester (12) by treatment with dilute $H_2O_2$. The benzoate ester is saponified by brief warming with aqueous NaOH in 2-methoxyethanol. The 4-amino-4-desoxy-10-alkyl-10-deazapteroic acid (13) so obtained is identical to that reported previously, DeGraw, Brown, Tagawa, Kisliuk, Gaumont and Sirotnak, J. Med. Chem. 25 1227 (1982). Coupling with diethyl L-glutamate followed by saponification of the diethyl ester (14) gives the target d,L or l,L diastereomer of 10-methyl-10-deazaminopterin. Chromatographic and spectral properties for the final products are likewise identical to those previously reported.

Substitution of other alkyl groups for $R_1$ as H and $R_2$ as $C_2H_5$ in the above scheme are apparent to those skilled in this art, with combinations of either hydrogen and alkyl or different alkyls as $R_1$ and $R_2$.

In Stage 1, the α-carbon atom of the propyl group of the benzoic acid group of the 10-deazaminopterin compound is alkylated by allyl bromide. The alkylation process requires prereaction of propyl benzoic acid with a lithium alkyl reagent in order to form an active anion reagent. In addition to propyl, and p-alkyl group can be alkylated having the structure:

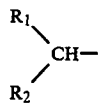

corresponding to the C10 alkyl group of the 10-DA with a free hydrogen atom. This process (which also causes ionization of the carboxyl group proton) requires lower temperatures at which it proceeds slowly, for example up to thirty hours. The reaction is preferably carried out under anhydrous conditions under argon in the presence of an inert polar solvent such as tetrahydrofuran. The presence of hexamethylphosphoric triamide (HMPA) cosolvent accelerates the ionization process. For example, in the case where $R_1$ and $R_2$ (of Formula III above) are both alkyl groups, HMPA cosolvent and a reaction temperature around 15° to 25° C. are required to obtain complete ionization within fifteen to thirty hours. After formation of the active anion, the allyl bromide can then be added slowly to the anion reagent reaction mixture, again at room temperature or below. Since the reactive anion is highly colored, and the reaction product is colorless, the reaction can be followed by discharge of color, and is complete when the reaction mixture is colorless. The solvents can then be removed, and the reaction product worked up.

In Stage 4 of the synthesis, degradation of the terminal carbon of the hexene (3) by oxidation with sodium periodate, catalyzed by $RuO_4$, results in an alkyl- and phenyl-substituted carboxylic acid having the desired 10-alkyl configuration of the 10-deazaminopterin at the 3-position of the acid. The reaction may be conducted at a temperature within the range from about 0° to about 50° C., but is preferably conducted at 0° to 5° C.

This carboxylic acid is resolved into its d, and l, isomers by crystallization of the d-α-methyl benzylamine or l-α-methyl benzylamine salts from an aliphatic alcohol solvent, such as isopropanol.

In Stages 5, 6 and 7, the d-acid, l-acid or racemic mixture is converted to the acid chloride, using $SOCl_2$ or other appropriate reagent, and then to the diazo ketone by reaction with diazomethane. This reaction proceeds at low temperature from 0° to 5° C. or below, in the presence of an inert solvent such as diethyl ether, and the diazo compound decomposed with HCl to form the chloromethyl ketone (7).

In Stage 8, the chloromethyl ketone is reacted with sodium azide to form the corresponding azido methyl ketone. This reaction proceeds at room temperature, but can be expedited with care and gentle warming. A polar solvent such as aqueous methanol assists in maintaining homogeneity of the reaction mixture. The desired ketone can be recovered from the mixture by solvent extraction using a water-immiscible solvent, such as chloroform.

In Stage 9, the azidomethyl ketone is converted to the aminomethyl ketone by hydrogenation in the presence of a catalyst such as palladium black. This is a conventional hydrogenation, and proceeds at room temperature. The aminomethyl ketone is isolated as the picrate, which is converted in Stage 10 to the semicarbazone.

In Stage 11, this reaction product is reacted with 2,4-diamino-5-nitro-6-chloropyrimidine in the presence of s-collidine, adding the pyrimidine at the 6-position to the amino group of the ketone (10). The semicarbazone is hydrolyzed in 90% $CF_3COOH$. Reduction of the nitro group with zinc dust in acetic acid causes ring closure to the dihydro pteridine which is oxidized in sito to the corresponding diamino pteridine ester with dilute $H_2O_2$. 1–5% $H_2O_2$ is preferred to prevent overoxidation to the N-oxide. The cyclization reaction proceeds at an acid pH, preferably within the range from 3 to 5, and consequently an acidic solvent such as aqueous acetic acid can be used. Aqueous acetic acid provides an acidic pH and the organic co-solvent effect of acetic acid aids in solubilizing. The reaction proceeds at moderately elevated temperatures within the range from 35° to 100° C., resulting in the formation of the pteroic acid ester.

In Stage 12, this ester is hydrolyzed to the free pteroic acid.

The resulting 2,4-diamino-4-desoxy-10-ethyl-10-deazapteroic acid is then converted to the 10-ethyl-10-deazaminopterin compound in two steps, Stages 13 and 14. First, the product is reacted with isobutyl chloroformate, and then with diethyl-L-glutamate, converting the pteroic acid group to the corresponding glutamide, diethyl ester, and the esterifying ethyl groups are then hydrolyzed by reaction with dilute aqueous alkali, such as aqueous sodium hydroxide, forming the glutamide free diacid group of the 10-deazaminopterin compound.

The Stage 13 reaction requires an acid acceptor to take up the liberated hydrogen chloride. The Stage 13 reaction may be conducted with other alkyl chloroformates such as methyl, ethyl, etc. Acid acceptors are preferably organic bases such as tertiary amines or substituted pyridines, for example, triethylamine, tributylamine, N-methylmorpholine, collidine and lutidine. The diethyl glutamate may be added as the free base or as the hydrochloride salt in the presence of an additional equivalent of the acid acceptor.

The reaction proceeds at room temperature or below, preferably 0° to −5° C. and an inert solvent can be used. The isobutyl chloroformate can be added slowly to the reaction mixture, and upon completion of the reaction, diethyl-L-glutamate, organic amine and more solvent can be added, and reaction continued at the same temperature until complete.

The reaction mixture is worked up by removing the solvent by evaporation, preferably in vacuo, and stirring the residue with a mildly alkaline aqueous solution, such as aqueous sodium bicarbonate. The diester is insoluble, and can be recovered by filtration, while unreacted pteroic acid dissolves in the alkaline solution.

Hydrolysis of the esterifying ethyl groups is carried out with aqueous alkali at room temperature or above. The diester can be dissolved in a suitable solvent, such as 2-methoxyethanol, and held in the presence of the aqueous alkali until hydrolysis is complete. The acidic 10-ethyl-10-deazaminopterin compound is soluble in aqueous alkali, and can then be precipitated by addition of acid, such as glacial acetic acid. The precipitate can be recovered, washed and dried.

The following Example describes the preparation of d, L and l, L 10-ethyl-10-deazaminopterin, using the above synthesis:

REFERENCE EXAMPLE I

Elemental analyses were obtained from Galbraith Laboratories, Knoxville, TN. The $^1H$ NMR spectra were taken on a Varian EM 360A or a JEOL FX90Q spectrometer. Mass spectra were run on a LKB 9000 GC-MS spectrometer. Ultraviolet spectra were taken on a Perkin-Elmer 552 spectrophotometer. TLC was carried out on Uniplates from Analtech coated with 250 μm of silica gel GF. Melting points were determined on a Thomas Hoover Uni-melt apparatus. Optical rotations were obtained on a Perkin-Elmer 141 polarimeter.

STAGES 1, 2 and 3

Preparation of 4-p-carboxyphenyl-1-hexene (2) and methyl ester (3)

To an ice-cold solution of diisopropylamine (8.5 ml, 0.061 mol) in 100 ml of dry tetrahydrofuran was added, dropwise, 45.6 ml (0.073 mol) of 1.6M butyl lithium, in hexane. The solution was chilled for 1 hour, when a solution of p-propylbenzoic acid (1) (5.0 g, 0.03 mol) in 30 ml of tetrahydrofuran was added dropwise, followed by 5.8 ml of HMPA. The mixture was kept at ambient temperature for 63 hours, and treated dropwise with 3.6 g (0.03 mol) of allyl bromide in 30 ml of tetrahydrofuran, to quench the color of the dark red dianion. The solvent was evaporated in vacuo and the residue partitioned between water (200 ml) and Et$_2$O (50 ml). After two additional Et$_2$O washes, the aqueous solution was acidified with 2N HCl to precipitate the product (2). The mixture was extracted with three 50 ml portions of CHCl$_3$, which was dried (MgSO$_4$) and evaporated, to leave 10 g of crude product (2) (contained HMPA).

The material was immediately esterified by stirring with 100 ml of 4.5% HCl in MeOH at room temperature for 42 hours. The solvent was removed in vacuo, and the residue taken up in 100 ml of CHCl$_3$, and washed with 25 ml of saturated NaHCO$_3$. The CHCl$_3$ was evaporated, and the residue dissolved in 100 ml of pentane. The solution was washed with water (25 ml), dried over MgSO$_4$, and evaporated to leave 4.1 g (63%) of the methyl ester (3), p-hexenyl-methyl benzoate, as a liquid; TLC (CHCl$_3$—MeOH, 9:1; silica gel) R$_f$ 0.90; NMR (CDCl$_3$) δ 0.80 (3H, t, CH$_3$), 1.70 (2H, m, CH$_2$CH$_3$), 2.50 (3H, m, allylic, benzylic H's), 3.90 (3H, s, OCH$_3$), 5.0 (3H, m, olefins), 7.25 (2H, d, 3', 5'—Ar), 8.00 (2H, d, 2', 6'—Ar).

A portion of the ester (3) was saponified (10% NaOH—MeOH, 1:7) and the liberated acid (2) was purified by preparative TLC (Silica gel, CHCl$_3$—MeOH, 9:1) to afford an analytical sample of (2) as a gum.

Anal C$_{13}$H$_{16}$O$_2$.¼H$_2$O.Calc % C, 74.8; H, 7.97. Found: C, 74.9; H, 8.14.

STAGE 4

Preparation of 3-p-carbomethoxyphenylvaleric acid (4)

A solution of the p-hexenyl methyl-benzoate (3) (21.0 g, 0.096 mol) in 990 ml of acetone was cooled in ice and a cold solution of NaIO$_4$ (103 g, 0.48 mol) in 660 ml of water containing 1.25 g of RuO$_4$ hydrate was added, to cause formation of a copious light green precipitate. The mixture was stirred for 10 min in the cold and another 20 min at room temperature. The mixture was filtered through a Celite pad, followed by a wash with 60% acetone. The filtrate was treated with 10 ml of isopropyl alcohol, kept at room temperature for 10 min, and saturated with NaCl. The mixture was extracted with 3–500 ml portions of CHCl$_3$, which were washed with 200 ml of brine, and extracted with 500 ml of 1.5N NH$_4$OH. The NH$_4$OH extract was acidified with concentrated HCl, and thrice extracted with 100 ml portions of CHCl$_3$. After drying over MgSO$_4$, the CHCl$_3$ was evaporated, to leave 17.5 g (77%) of the racemic product (4) as a brown partially crystalline syrup; NMR (CDCl$_3$) δ 0.82 (3H, t, CH$_3$), 1.73 (2H, m, —CH$_2$CH$_3$), 2.60 (2H, m, CH$_2$COOH), 3.90 (3H, s, —OCH$_3$), 7.33 (2H, d, 3', 5'—Ar), 8.10 (2H, d, 2', 6'—Ar). The racemic acid was separated into the d- and l-isomers as the salt with d or l-α-methylbenzylamine, as described below.

Four crystallizations from isopropanol of the salt of (4) with d-α-methylbenzylamine gave white crystals, mp 165°–166° C. Anal. C$_{21}$H$_{27}$NO$_4$ (C, H, N). Liberation of the free d-acid by partition between 1N HCl and CHCl$_3$ afforded a gum, [α]$_D$+22.7° (CHCl$_3$).

The mother liquors from the first crystallization were evaporated, and the free acid liberated as above. The salt prepared from an equivalent of l-α-methylbenzylamine was crystallized twice from isopropanol, to give white crystals, mp 164°–165° C. The free l-acid showed a rotation of [α]$_D$−24.1°.

STAGES 5, 6 and 7

Preparation of 1-Chloro-4-p-carbomethoxyphenyl-2-hexanone (7)

A solution of the racemic acid (4) (or the d- or l-isomer of (4)) (5.9 g, 0.025 mol) in 30 ml of benzene containing 38 ml of SOCl$_2$ was heated under reflux for 1 hour. The solvent was removed in vacuo, and the residual acid chloride dissolved in 20 ml of Et$_2$O. The solution was added dropwise at 0°–5° C. to an ethereal solution of diazomethane (from 22.6 g of nitrosomethyl urea). The yellow solution of the incipient diazo ketone was treated with gaseous HCl for 30 min, and poured into 135 ml of ice H$_2$O. The Et$_2$O phase was separated, and washed with cold 0.5N Na$_2$CO$_3$ (25 ml), H$_2$O (25 ml) and dried over MgSO$_4$. Evaporation of solvent afforded 5.9 g (88%) of a yellow oil; TLC (silica gel; CHCl$_3$—MeOH, 40:1) R$_f$ 0.75 single spot; NMR (CDCl$_3$) δ 0.80 (3H, t, CH$_3$), 1.73 (2H, m, CH$_2$CH$_3$), 2.97 (2H, m, —CH$_2$C=O), 3.20 (1H, m, Ar—CH), 3.90 (3H, s, OCH$_3$), 3.95 (2H, s, CH$_2$Cl), 7.30 (2H, d, 3', 5'—ArH), 8.10 (2H, d, 2', 6'—ArH).

The optically resolved d and l isomers of (4) were carried through the same processes described for the chloromethyl ketone preparation, and all subseqent steps as described below. Physical and chromatographic properties were equal to those of their racemic counterparts, except as noted.

STAGE 8

Preparation of 1-azido-4-p-carbomethoxyphenyl-2-hexanone (8)

A mixture of the chloromethyl ketone (7, 5.9 g, 0.022 mol), 10.8 g (0.16 mol) of NaN$_3$ and 180 ml of 80% MeOH was stirred at room temperature for 20 hours. After evaporation of MeOH the aqueous residue was diluted to 100 ml with H$_2$O and extracted with three 50 ml portions of CHCl$_3$. The CHCl$_3$ was dried (MgSO$_4$) and evaporated to leave 5.5 g (91%) of a yellow oil (8); TLC (silica gel, CHCl$_3$0C$_6$H$_6$, 1:1) R$_f$ 0.30 single spot; IR cm$^{-1}$ 2105 (—N$_3$); NMR (CDCl$_3$) δ 0.80 (3H, t, CH$_3$), 1.70 (2H, m, CH$_2$CH$_3$), 2.80 (2H, m, CH$_2$C=O), 3.15 (1H, m, Ar—CH), 3.77 (2H, s, CH$_2$N$_3$), 3.90 (3H, s, OCH$_3$), 7.30 (2H, d, 3', 5'—ArH), 8.05 (2H, d, 2', 6'—ArH).

STAGE 9

Preparation of 1-Amino-4-p-carbomethoxyphenyl-2-hexanone Picrate (9)

A mixture of the azide ((8), 5.50 g, 0.02 mol), 3.05 ml (0.037 mol) of 12N HCl, 1.88 g of palladium black and 100 ml of EtOH was stirred under an atmosphere of $H_2$ for 6 hours. The catalyst was removed by filtration, and the filtrate was evaporated in vacuo to leave a yellow foam (5.6 g). This residue was treated with 50 ml of $H_2O$ and stirred until homogeneous. The aqueous supernatant was decanted from some insoluble gum and added to a warm solution of picric acid (5.0 g) in 275 ml of $H_2O$ with stirring. The yellow crystalline precipitate (9) was collected washed with $H_2O$ and dried to leave 6.70 g (70%), mp 144°–145° C. An analytical sample, mp 162°–163° C., was obtained by recrystallization from EtOH.

Anal. $C_{20}H_{22}N_4O_{10}$(C, H, N). (9) d-isomer, mp 129°–131° C. (9). l-isomer mp 125°–130° C.

STAGE 10

Preparation of 1-amino-4-p-carbomethoxyphenyl-2-hexanone semicarbazone picrate (10)

A mixture of the amino ketone picrate ((9) 6.4 g, 0.133 mol), semicarbazide.HCl (2.6 g, 0.023 mol) and 190 ml of 70% EtOH was stirred at room temperature for 90 hours. The solid was collected and washed with 70% EtOH, and the filtrate was evaporated and similarly retreated with 1.27 g of semicarbazide.HCl in 75 ml of 70% EtOH to afford 0.76 g of yellow crystals (10), mp 200°–201° C. The original solid above was treated with 225 ml of warm EtOH and the insoluble portion collected to give 2.67 g, ml 196°–197° C. The combined mother liquors were evaporated and retreated with 0.84 g of semicarbazide.HCl in 61 ml of 70% EtOH to afford another 1.66 g of (10), mp 200°–201° C., for a total yield of (10) of 5.09 (71%).

Anal. $C_{21}H_{25}N_7O_{10}$(C, H, N). (10) d-isomer mp 196°–197° C., (10) l-isomer, mp 196°–196.5° C.

When the picrate salts were stirred with a ten-fold excess of Dowex 2 (×8) chloride resin in 75% EtOH, followed by filtration and evaporation of solvent, the respective hydrochloride salts were obtained in quantitative yield as white crystals; (10).HCl, mp 187°–191°.

STAGE 11

Preparation of 1-(2',4'-diamino-5'-nitro-6'-pyrimidinyl)amino-4-p-carbomethoxyphenyl-2-hexanone Trifluoroacetate (11)

To a solution of sodium ethoxide (from 219 mg, 0.0095 g atm Na) in EtOH (69 ml) was added 3.3 g (0.0095 mol) of the semicarbazone.HCl (10). The mixture was stirred at room temperature for 30 min and evaporated to dryness in vacuo. The residue was taken up in 170 ml of dry DMF and treated with 1.89 g (0.01 mol) of 2,4-diamino-5-nitro-6-chloropyrimidine and 1.26 ml (0.0095 mol) of s-collidine. The mixture was stirred at 90°–100° for 30 min and evaporated in vacuo. The residue was stirred with 225 ml of ice water and the yellow solid semicarbazone intermediate collected and dried to leave 2.86 g.

The material was stirred with 48 ml of 90% trifluoroacetic acid for 18 hours and the solvent removed in vacuo. The residue was treated with 50 ml of water and the pH adjusted to 8.9 with 15% $K_2CO_3$. The mixture was stirred 15 min and the supernatant decanted from the gummy solid, which was washed with 50 ml of water. The solid was taken up to 100 ml of hot 2-methoxyethanol and some insoluble material removed by filtration, followed by evaporation of the filtrate to afford 2.90 g. This material was redissolved in 5 ml of 2-mthoxyethanol and applied to a column of 90 g of Baker Flash Chromatography silica gel. The column was preeluted by $CHCl_3$ and the product removed with $CHCl_3$—MeOH, 93:7 to yield 1.11 g (44%) of a foamy solid (11). A portion was crystallized from 50% EtOH—$Et_2O$ for analysis, mp 73° C.; NMR ($CDCl_3$) δ 0.80 (3H, t, $CH_3$), 1.75 (2H, m, $CH_2CH_3$), 2.85 (2H, m, $CH_2C=O$), 3.25 (1H, m, Ar—$CH$), 3.90 (3H, s, $OCH_3$), 4.20 (2H, d, —$NHCH_2C=O$), 6.50 (2H, m, $NH_2$), 7.35 (2H, m, 3', 5'—ArH), 8.05 (2H, d, 2', 6'—ArH), 9.00 (2H, m, $NH_2$), 9.80 (1H, t, $NHCH_2$). Anal. $C_{18}H_{22}N_6O_5.\frac{3}{4}CF_3COOH.\frac{3}{4}H_2O$ (C, H, N, F).

STAGE 12

Methyl 2,4-diamino-4-deoxy-10-ethyl-10-deazapteroate (12)

A solution of 1.52 g (0.0038 mol) of the nitro ketone (11) in 33 ml of HOAc was stirred at 90°–100° C., while Zn dust (1.5 g) was added portionwise over 30 min. The mixture was stirred another 15 min at 90°–100° C., cooled to room temperature, and filtered. The filter cake was washed with 17 ml of 50% HOAc, and the combined filtrate and wash were treated with 1.3 ml of 30% $H_2O_2$. After 1 hour the solvent was removed under vacuum, and the residue treated with 65 ml of $H_2O$. The pH was adjusted to 8 with concentrated $NH_4OH$, and the mixture was stirred overnight. The precipitate was collected, washed thoroughly with $H_2O$, and dried, to afford 1.11 g (83%) of pale yellow crystals (12); TLC ($CHCl_3$—MeOH, 9:1) single uv spot, $R_f$ 0.40; NMR (DMSO—$d_6$) o 0.78 (3H, t, $CH_3$), 1.70 (2H, m, $CH_2CH_3$), 3.20 (3H, m, C—9, 10H's), 3,85 (3H, s, $OCH_3$), 6.70 (2H, S, $NH_2$), 7.33 (2H, d, 3', 5'—ArH), 7.60 (2H, m, $NH_2$), 7.83 (2H, d, 2', 6'—ArH), 8.37 (1H, s, C—7H). Anal $C_{18}H_{20}N_6O_2.\frac{1}{2}H_2O$ (C, H, N).

STAGE 13

Preparation of 2,4-diamino-4-desoxy-10-ethyl-10-deazapteroic acid (13)

A solution of 1.17 g of the diamino ester (12) in 36 ml of 2-methoxyethanol was warmed to 100° C. and 2.71 ml of 10% NaOH was added. Heating was continued for 15 min, and the solvent was evaporated in vacuo. The residue was dissolved in 35 ml of $H_2O$, and adjusted to pH 5–6 with concentrated HCl. The precipitate was collected, washed with $H_2O$ and EtOH, and dried, to leave 0.90 g (80%) of pale yellow crystals (13); HPLC ($C_{18}$ Bondapak reverse phase, MeOH-0.1M $KH_2PO_4$ (pH 6.7), 1:3) 98% pure, uv max at pH 13 235 nm, 255, 370; NMR ($Me_2SO$—$d_6$) δ 0.74 (3H, t, $CH_3$), 1.70 (2H, m, $CH_2CH_3$), 3.10 (3H, m, C—9, 10H's), 6.56 (2H, s, $NH_2$), 7.31 (2H, d, 3', 5'—ArH), 7.50 (2H, br, s, $NH_2$), 7.80 (2H, d, 2', 6'—ArH), 8.34 (1H, s, C—7H). The HPLC, UV and NMR were identical to those measured for (13) previously reported (DeGraw, Brown, Tagawa, Kisliuk, Gaumont and Sirotnak, *J. Med. Chem.* 25, 1227 (1982)).

Coupling of the acid (13) with diethyl L-glutamate and saponification of the intermediate ester (14) to yield the resolved d,L-and l,L-diastereomeric acids (15) was carried out via the procedure reported in *J. Med. Chem.* 25, 1227 (1982).

The d,L and l,L-alkyl-10-deazaminopterin can be administered per se, or in association with a pharmaceutically acceptable diluent or carrier. The invention accordingly also provides a pharmaceutical composition in dosage unit form comprising from 0.1 to about 500 mg of d,L- or l,L-10-alkyl-10-deazaminopterin or racemic mixture thereof per dosage unit, together with a pharmaceutically acceptable nontoxic inert carrier or diluent therefor.

The d,L- or l,L-10-alkyl-10-deazaminopterin or racemic mixture thereof can be used as such, or in the form of an acid addition salt. These salts are formed with one or more free $NH_2$ groups of the 10-deazaminopterin molecule.

The acid addition salts are preferably the pharmaceutically acceptable, nontoxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicyclic, o-acetyloxybenzoic, nicotinic and isonicotinic acid, and organic sulphonic acids, for example, methanesulphonic, ethanesulphonic, 2-hydroxyethanesulphonic, toluene-p-sulphonic, and naphthalene-2-sulphonic acid.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

The d,L- or l,L-10-alkyl-10-deazaminopterin or racemic mixture thereof or salt thereof can be administered to the animal by an available route, including oral and parenteral (intravenous, intraperitoneal, subcutaneous, and intramuscular) administration. The amount administered is sufficient to ameliorate the leukemia or the ascitic tumor of rheumatoid arthritis, and will depend upon the type of leukemia or rheumatoid arthritis, the species of animal, and the weight of the animal. For example, in human administration, a dosage of d,L or l,L-10-ethyl-10-deazaminopterin or racemic mixture thereof in within the range from about 0.1 mg/kg to about 500 mg/kg per day should be sufficient. Dosages in the higher part of the range, approaching 500 mg/kg, are normally administered in conjunction with leucovoran (di-5-formyl tetrahydrofolate) to reduce toxicity. In the treatment of lower test animals, a similar dosage range is therapeutic. The upper limit of dosage is that imposed by toxic side effects, and can be determined by trial and error for the animal to be treated, including humans.

To facilitate administration, the d,L- or l,L-10-alkyl-10-deazaminopterin or racemic mixture thereof or salt thereof can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the d,L- or l,L-10-alkyl-10-deazaminopterin or racemic mixture thereof. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl- and propyl-hydroxybenzoate, talc or magnesium stearate.

For convenience in handling, the d,L- or l,L-10-alkyl-10-deazaminopterin or racemic mixture thereof and carrier or diluent can be enclosed or encapsulated in a capsule, sachet, cachet, gelatin, paper or other container, especially when intended for use in dosage units. The dosage units can for example take the form of tablets, capsules, suppositories or cachets.

The following Examples illustrate various forms of dosage units in which the d,L- or l,L-10-alkyl-10-deazaminopterin or racemic mixture thereof or salts thereof can be prepared, exemplified in each composition as the 10-ethyl compounds.

EXAMPLE 1

| Tablet formulation | Mg/tablet |
|---|---|
| d, L- or 1, L-10-ethyl-10-deazaminopterin or racemic mixture thereof | 15 |
| Lactose | 86 |
| Corn starch (dried) | 45.5 |
| Gelatin | 2.5 |
| Magnesium stearate | 1.0 |

The d,L- or l,L-10-ethyl-10-deazaminopterin or racemic mixture thereof is powdered and passed through a mesh sieve and well mixed with the lactose and 30 mg of the corn starch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE 2

| Tablet formulation | Mg/tablet |
|---|---|
| d, L-or 1, L-10-ethyl-10-deazaminopterin or racemic mixture thereof | 100 |
| Lactose | 39 |
| Corn Starch (dried) | 80 |
| Gelatin | 4.0 |

-continued

| Tablet formulation | Mg/tablet |
|---|---|
| Magnesium stearate | 2.0 |

The method of preparation is identical with that of Example 1 except that 60 mg of starch is used in the granulation process and 20 mg during tabletting.

EXAMPLE 3

| Capsule formulation | Mg/capsule |
|---|---|
| d, L- or l, L-10-ethyl-10-deazaminopterin or racemic mixture thereof | 250 |
| Lactose | 150 |

The d,L- or l,L-10-ethyl-10-deazaminopterin or racemic mixture thereof and lactose are passed through a sieve and the powders well mixed together before filling into hard gelatin capsules of suitable size, so that each capsule contains 400 mg of mixed powders.

EXAMPLE 4

| Suppositories | Mg/suppositories |
|---|---|
| d,L- or l,L-10-ethyl-10-deazaminopterin or racemic mixture thereof | 50 |
| Oil of Theobroma | 950 |

The d,L- or l,L-10-ethyl 10-deazaminopterin or racemic mixture thereof is powdered and passed through a sieve and triturated with molten oil of theobroma at 45° C. to form a smooth suspension.

The mixture is well stirred and poured into molds, each of nominal 1 g capacity, to produce suppositories.

EXAMPLE 5

| Cachets | Mg/cachet |
|---|---|
| d,L- or l,L-10-ethyl-10-deazaminopterin or racemic mixture thereof | 100 |
| Lactose | 400 |

The d,L- or l,L-10-ethyl-10-deazaminopterin or racemic mixture thereof is passed through a mesh sieve, mixed with lactose previously sieved and fitted into cachets of suitable size so that each contains 500 mg.

EXAMPLE 6

| Intramuscular injection (sterile suspension in aqueous vehicle) | Mg |
|---|---|
| d,L- or l,L-10-ethyl-10-deazaminopterin or racemic mixture thereof | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE 7

| Intraperitoneal intraveneous or subcutaneous injection (sterile solution in aqueous carrier system) | Mg |
|---|---|
| d,L- or l,L-10-ethyl-10-deazaminopterin or racemic mixture thereof, hydrochloric acid addition salt | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

Following the test procedure outlined by DeGraw et al, *J. Med. Chem.* 25, 1227 (1982), biochemical and transport properties in L1210 cells for the d,L and l,L forms of 10-ethyl-10-deazaminopterin in comparison with methotrexate were determined. The results are shown in Table I.

TABLE I

Biochemical and Growth Inhibition Data Derived with L1210 Cells[1]

| Isomer of 10-Deazaminopterin | Dihydrofolate Reductase inhibn (Ki)[2], pM | growth inhibn (minimum inhibitory concentration$_{50}$)[3], nM | transport[2] influx Km, µM | efflux k, min$^{-1}$ |
|---|---|---|---|---|
| l, L-10-methyl | 3.17 | 1.18 | 1.90 | 0.267 |
| d, L-10-methyl | 4.24 | 0.68 | 1.91 | 0.258 |
| l, L-10-ethyl | 12.40 | 1.52 | 1.62 | 0.249 |
| d, L-10-ethyl | 3.93 | 0.43 | 1.58 | 0.253 |
| Control (methotrexate) | 4.42 | 2.48 | 5.61 | 0.213 |

[1]Average of 3-6 runs; standard error less than 15%
[2]See J. Med. Chem. 25 1227 (1982) for methods
[3]See F. Sirotnak, et al. Biochem. Pharmacol. 28,2993 (1979)

All of the diastereomers showed similar affinities for the transport protein of L1210. The Michaelis constant (Km) values were about $1.9 \times 10^{-6}$ M for the 10-methyl diastereomers and $1.6 \times 10^{-6}$ M for the 10-ethyl diastereomers. All had considerably stronger affinities than methotrexate at $5.6 \times 10^{-6}$ M, and similar ratios as previously observed[1] for the racemates. Likewise, the efflux rate constants (k) were very similar for all compounds, including methotrexate. For inhibition of dihydrofolate reductase derived from L1210, the d,L and l,L diastereomeric forms of 10-methyl-10-deazaminopterin were not significantly different from one another or MTX, with Ki values in the $3-4 \times 10^{-12}$ range. However, there was a three-fold difference between l,L and d,L isomers of 10-ethyl-10-deazaminopterin, with the latter also approximating MTX. This factor of three difference was also reflected in the inhibition of growth for L1210 cells, with the l,L isomer being only one-third as potent as the d,L isomer. There was not a significant difference observed between the 10-methyl d,L and l,L isomers in the growth inhibition.

Comparisons of the d,L and l,L diastereomers and racemic mixtures of 10-ethyl-10-deazaminopterin with regard to their abilities to inhibit growth of folate-dependent bacteria *Streptococcus faecium* and *Lactobacillus casei* are reported in Table II, together with the 7,8-dihydro and 5,6,7,8-tetrahydro forms of these compounds, as well as data on the inhibitory potencies ($IC_{50}$) against the dihydrofolate reductases derived from *L. casei* and chicken liver.

was intermediate between the values for the resolved d,L and l,L diastereomers.

The d,L and l,L isomers of 10-ethyl-10-deazaminopterin and the racemic mixture were also evaluated in vivo against L1210 leukemia in mice.

Sodium hydroxide (0.2 ml of 0.1N) was added to 5 mg of the 10-ethyl-10-deazaminopterin isomer, d,L or l,L or the racemic mixture. Distilled water was then added, the pH adjusted to 7.0, and the solution then

TABLE II

| | Bacterial Growth and Enzyme Inhibition[1] | | | |
|---|---|---|---|---|
| | (Minimum Inhibitory Concentration$_{50}$)[2,5] ng/ml for growth inhibition | | DHFR inhibition (inhibitory conentration for 50% inhibition), nm | |
| Isomer of 10-ethyl-10-Deazaminopterin | *S. faecium* American Type Culture Collection 8043 | *L. casei* American Type Culture Collection 7469 | *L. casei*[3] | chicken liver[4] |
| l, L | 2.2 | 0.23 | 38 | 22 |
| d, L | 3.9 | 0.29 | 14 | 19 |
| racemic mixture | 2.7 | 0.26 | 22 | 20 |
| 7,8-dihydro l, L[6] | 1.1 | 0.165 | 120 | 50 |
| 7,8-dihydro d, L[6] | 1.1 | 0.027 | 25 | 26 |
| 7,8-racemic dihydro mixture[6] | 1.1 | 0.055 | 32 | 34 |
| 5,6,7,8-tetrahydro l, L[7] | 3.1 | 0.30 | 120 | 76 |
| 5,6,7,8-tetrahydro d, L[7] | 2.5 | 0.08 | 35 | 20 |
| 5,6,7,8-tetrahydro racemic mixture[7] | 2.6 | 0.14 | 50 | 34 |
| Control (methotrexate) | 0.4 | 0.013 | 10 | 19 |

[1] See J. Med. Chem. 17,552 (1974)
[2] Folate concentration = 1 ng/mL
[3] Enzyme derived from *L. casei*
[4] Enzyme derived from chicken liver
[5] All compounds were weak inhibitors or inactive against methotrexate-resistant strains of these bacteria
[6] UVpH 7.4 292 nm, 324; reduced with $Na_2S_2O_4$
[7] UVpH 7.4 296 nM, reduced with $H_2$—$PtO_2$ Against *S. faecium*, the l,L-isomer was slightly more potent than the d,L-isomer. Reduction to the dihydroform caused an increase in potency, with no difference observed among the compounds. Further reduction to tetrahydro derivatives caused the inhibitory potencies to return to the range seen for the fully aromatic substrates, but with a reversal in the l,L to d,L relationship, the d,L isomer now being slightly more potent than the l,L isomer. In *L. casei*, the compounds were more active by an order of magnitude. Again, little difference was noted among the unreduced inhibitors. However, the dihydro d,L-isomer was about 11 times more active than the precursor, and 6 times more active than the corresponding dihydro l,L-isomer. Further reduction to tetrahydro caused activity to decrease, but the superiority of the d,L isomer was maintained.

Inhibition of the dihydrofolate reductases derived from *L. casei* and chicken liver was fairly similar among the isomers and the methotrexate control. A notable difference is the approximately three-fold greater potency of the d,L-isomer over the l,L-isomer against the *L. casei* enzyme. Reduction decreased potencies, but only slightly in the d,L-series. In all cases involving the enzymes or whole cell inhibitions the racemic mixture diluted with distilled water to 10 ml. The resulting solution and dilutions thereof were administered in aliquots of 0.1 ml by intraperitoneal injection into L1210 leukemic BD (2) $F_1$ female mice (A. R. Schmid, Madison, Wis.). Injections were given once per day, three times per week (Monday, Wednesday, Friday) starting one day after tumor transplantation ($10°$ cells/mouse). Therapy was continued until death of the animals.

For comparison purposes, and as a control, a parallel series of tests was carried out simultaneously using L1210 leukemic BD (2) $F_1$ female mice, under exactly the same test conditions, administering methotrexate (MTX) instead of 10-deazaminopterin.

The procedure for testing, and the maintenance and transplantation of the L1210 leukemia, is in accordance with the method of Hutchinson, D. J., Robinson, D. C., Martin, D., Ittensohn, O. L. and Dillenberg, *Journal Cancer Res.* 22 57–72 (1962). The antileukemic activity of the 10-deazaminopterin isomer, d,L or l,L or the racemic mixture, was evaluated against methotrexate in terms of the increase in median life span obtained at various dosages, up to the maximum tolerated level, when compared to untreated controls. Toxicity of various dosages was evaluated by the extent of weight loss and eventual death, with no evidence of tumor. The data are given in Table III.

TABLE III

| | Antitumor Activity Against L1210 Leukemia in Mice | | | |
|---|---|---|---|---|
| Compd[1] | dose (mg/kg) | Mean Survival Time (days) | Increased Life Span (%) | 30-day survivors observed/total | Toxic deaths no/total |
| control | — | 6.6 | 0 | 0/5 | 0/5 |

TABLE III-continued

Antitumor Activity Against L1210 Leukemia in Mice

| Compd[1] | dose (mg/kg) | Mean Survival Time (days) | Increased Life Span (%) | 30-day survivors observed/total | Toxic deaths no/total |
|---|---|---|---|---|---|
| d, L | 9 | 18.3 ± 1.7 | +177 | 0/6 | 0/6 |
| | 12 | 19.8 ± 2.3 | +199 | 0/9 | 3/9 |
| | 18 | 17.5 ± 1.5 | >+165 | 1/9 | 5/9 |
| | 24 | 10.0 ± 0 | +55 | 0/3 | 3/3 |
| l, L | 12 | 15.7 ± 0.5 | +138 | 0/3 | 0/3 |
| | 18 | 17.3 ± 0.7 | +163 | 0/9 | 0/9 |
| | 24 | 19.0 ± 1.0 | +187 | 0/9 | 0/9 |
| | 32 | 18.8 ± 2.2 | +181 | 0/6 | 1/6 |
| racemic mixture | 9 | 15.5 ± 0.6 | +135 | 0/10 | 0/10 |
| | 12 | 16.7 ± 0.7 | +153 | 0/10 | 0/10 |
| | 18 | 19.3 ± 0.8 | +193 | 0/10 | 0/10 |
| | 24 | 20.3 ± 1.9 | >+207 | 2/10 | 2/10 |
| | 32 | 16.0 ± 1.1 | +67 | 0/10 | 10/10 |
| methotrexate | 9 | 15.7 ± 0.4 | +137 | 0/10 | 0/10 |
| | 12 | 16.3 ± 0.7 | +147 | 0/10 | 1/10 |
| | 18 | 14.5 ± 1.6 | +119 | 0/10 | 6/10 |
| | 24 | 9.6 ± 1.1 | +46 | 0/10 | 10/10 |

[1] Drug given sc (every 2 days times 5) 24 h after $10^6$ cells implanted ip.

The data show no significant difference in the percentage increase in life span among the test compounds. The results clearly indicate however that the l,L-isomer is approximately one-half as toxic as the d,L-isomer.

In general, the data in Tables I, II and III show the d,L-isomers can be generally more inhibitory than the l,L-isomers in the various in vitro assays. While the continued use of the equal diastereomeric or racemic mixture of 10-ethyl-10-deazaminopterin is acceptable, the use of the d,L-isomer is to be preferred when a lower dose is desired, to obtain the same degree of effectiveness. On the other hand, in view of the lower toxicity of the l,L isomer, larger doses of this isomer can be administered, with an accompanying increased effectiveness, than the d,L-isomer.

Having regard to the foregoing disclosure, the following is claimed as inventive and patentable embodiments thereof:

1. The resolved d,L and l,L-diastereomers of 10-alkyl-10-deazaminopterin compounds having the formula:

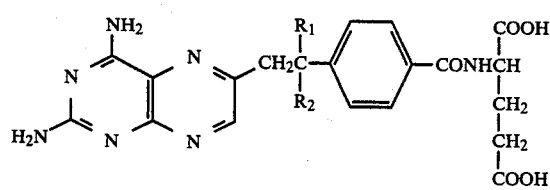

wherein:

$R_1$ and $R_2$ are both selected from the group consisting of hydrogen and alkyl having from one to about eight carbon atoms, $R_1$ is different from $R_2$, and at least one of $R_1$ and $R_2$ is alkyl.

2. The resolved d,L and l,L-diastereomers of 10-alkyl-10-deazaminopterin compounds according to claim 1 in which one of $R_1$ and $R_2$ is alkyl and the other is hydrogen.

3. The resolved d,L and l,L-diastereomers of 10-alkyl-10-deazaminopterin compounds according to claim 2 in which the alkyl is ethyl.

4. The resolved d,L and l,L-diastereomers of 10-alkyl-10-deazaminopterin compounds according to claim 2 in which the alkyl is methyl.

5. 10-Deazaminopterin compounds according to claim 1 in which both of $R_1$ and $R_2$ are different alkyl.

6. d,L-10-ethyl-10-deazaminopterin.

7. l,L-10-ethyl-10-deazaminopterin.

8. A pharmaceutical composition in dosage unit form for treating leukemia or an ascites tumor comprising an amount within the range from about 0.1 to about 500 mg of d,L-10-ethyl-10-deazaminopterin per dosage unit therapeutically effective to ameliorate leukemia or the ascites tumor, together with a pharmaceutically acceptable nontoxic carrier or diluent therefor.

9. A pharmaceutical composition according to claim 8 in which the d,L-10-ethyl-10-deazaminopterin is in the form of a pharmaceutically acceptable acid addition salt.

10. A pharmaceutical composition in tablet form for treating leukemia or an ascites tumor comprising an amount within the range from about 0.1 to about 500 mg of d,L-10-ethyl-10-deazaminopterin per tablet therapeutically effective to ameliorate leukemia or the ascites tumor, together with a pharmaceutically acceptable nontoxic carrier or diluent therefor.

11. A pharmaceutical composition according to claim 10 in which the d,L-10-ethyl-10-deazaminopterin is in the form of a pharmaceutically acceptable acid addition salt.

12. A pharmaceutical composition in capsule form for treating leukemia or an ascites tumor comprising an amount within the range from 0.1 to about 500 mg of d,L-10-ethyl-10-deazaminopterin per capsule therapeutically effective to ameliorate leukemia or the ascites tumor, together with a pharmaceutically acceptable nontoxic inert carrier or diluent therefor.

13. A pharmaceutical composition according to claim 12 in which the d,L-10-ethyl-10-deazaminopterin is in the form of a pharmaceutically acceptable acid addition salt.

14. A pharmaceutical composition in suppository form for treating leukemia or an ascites tumor comprising an amount within the range from about 0.1 to about 500 mg of d,L-10-ethyl-10-deazaminopterin per suppository therapeutically effective to ameliorate leukemia or the ascites tumor, together with a pharmaceutically acceptable nontoxic inert carrier or diluent therefor.

15. A pharmaceutical composition according to claim 14 in which the d,L-10-ethyl-10-deazaminopterin is in the form of a pharmaceutically acceptable acid addition salt.

16. A pharmaceutical composition in cachet form for treating leukemia or an ascites tumor comprising an amount within the range from about 0.1 to about 500 mg of d,L-10-ethyl-10-deazaminopterin per cachet therapeutically effective to ameliorate leukemia or the ascites tumor, together with a pharmaceutically acceptable nontoxic inert carrier or diluent therefor.

17. A pharmaceutical composition according to claim 16 in which the d,L-10-ethyl-10-deazaminopterin is in the form of a pharmaceutically acceptable acid addition salt.

18. A pharmaceutical composition in sterile aqueous form for treating leukemia or an ascites tumor comprising an amount within the range from about 0.1 to about 500 mg of d,L-10-ethyl-10-deazaminopterin therapeutically effective to ameliorate leukemia or the ascites tumor, together with a pharmaceutically acceptable nontoxic sterile inert aqueous carrier or diluent therefor.

19. A pharmaceutical composition according to claim 18 in which the d,L-10-ethyl-10-deazaminopterin is in the form of a pharmaceutically acceptable acid addition salt.

20. A pharmaceutical composition according to claim 18 in aqueous solution form.

21. A pharmaceutical composition according to claim 18 in aqueous dispersion form.

22. A pharmaceutical composition in dosage unit form for treating leukemia or an ascites tumor comprising an amount within the range from about 0.1 to about 500 mg of 1,L-10-ethyl-10-deazaminopterin per dosage unit therapeutically effective to ameliorate leukemia or the ascites tumor, together with a pharmaceutically acceptable nontoxic carrier or diluent therefor.

23. A pharmaceutical composition according to claim 22 in which the 1,L-10-ethyl-10-deazaminopterin is in the form of a pharmaceutically acceptable acid addition salt.

24. A pharmaceutical composition in tablet form for treating leukemia or an ascites tumor comprising an amount within the range from about 0.1 to about 500 mg of 1,L-10-ethyl-10-deazaminopterin per tablet therapeutically effective to ameliorate leukemia or the ascites tumor, together with a pharmaceutically acceptable nontoxic carrier or diluent therefor.

25. A pharmaceutical composition according to claim 24 in which the 1,L-10-ethyl-10-deazaminopterin is in the form of a pharmaceutically acceptable acid addition salt.

26. A pharmaceutical composition in capsule form for treating leukemia or an ascites tumor comprising an amount within the range from 0.1 to about 500 mg of 1,L-10-ethyl-10-deazaminopterin per capsule therapeutically effective to ameliorate leukemia or the ascites, together with a pharmaceutically acceptable nontoxic inert carrier or diluent therefor.

27. A pharmaceutical composition according to claim 26 in which the 1,L-10-ethyl-10-deazaminopterin is in the form of a pharmaceutically acceptable acid addition salt.

28. A pharmaceutical composition in suppository form for treating leukemia or an ascites tumor comprising an amount within the range from about 0.1 to about 500 mg of 1,L-10-ethyl-10-deazaminopterin per suppository therapeutically effective to ameliorate leukemia or the ascites tumor, together with a pharmaceutically acceptable nontoxic inert carrier or diluent therefor.

29. A pharmaceutical composition according to claim 28 in which the 1,L-10-ethyl-10-deazaminopterin is in the form of a pharmaceutically acceptable acid addition salt.

30. A pharmaceutical composition in cachet form for treating leukemia or an ascites tumor comprising an amount within the range from about 0.1 to about 500 mg of 1,L-10-ethyl-10-deazaminopterin per cachet therapeutically effective to ameliorate leukemia or the ascites tumor, together with a pharmaceutically acceptable nontoxic inert carrier or diluent therefor.

31. A pharmaceutical composition according to claim 30 in which the 1,L-10-ethyl-10-deazaminopterin is in the form of a pharmaceutically acceptable acid addition salt.

32. A pharmaceutical composition in sterile aqueous form for treating leukemia or an ascites tumor comprising an amount within the range from about 0.1 to about 500 mg of 1,L-10-ethyl-10-deazaminopterin therapeutically effective to ameliorate leukemia or the ascites tumor, together with a pharmaceutically acceptable nontoxic sterile inert aqueous carrier or diluent therefor.

33. A pharmaceutical composition according to claim 32 in which the 1,L-10-ethyl-10-deazaminopterin is in the form of a pharmaceutically acceptable acid addition salt.

34. A pharmaceutical composition according to claim 32 in aqueous solution form.

35. A pharmaceutical composition according to claim 32 in aqueous dispersion form.

36. A process for treating leukemia and ascites tumors which comprises administering to a warm-blooded animal having an abnormal proportion of leukocytes or other evidence of the malignancy, a therapeutic and relatively nontoxic amount of d,L-10-ethyl-10-deazaminopterin, to ameliorate leukemia or ascites tumors.

37. A process according to claim 36 in which the d,L-10-ethyl-10-deazaminopterin is administered as a pharmaceutically acceptable salt thereof.

38. A process according to claim 36 in which the d,L-10-ethyl-10-deazaminopterin is administered in an amount within the range from about 0.1 to about 500 mg per day.

39. A process according to claim 36 in which the d,L-10-ethyl-10-deazaminopterin is administered with an inert diluent or carrier.

40. A process according to claim 36 in which the d,L-10-ethyl-10-deazaminopterin is administered orally.

41. A process according to claim 36 in which the d,L-10-ethyl-10-deazaminopterin is administered parenterally.

42. A process for treating leukemia and ascites tumors which comprises administering to a warm-blooded animal having an abnormal proportion of leukocytes or other evidence of the malignancy, a therapeutic and relatively nontoxic amount of 1,L-10-ethyl-10-deazaminopterin, to ameliorate leukemia or ascites tumors.

43. A process according to claim 42 in which the 1,L-10-ethyl-10-deazaminopterin is administered as a pharmaceutically acceptable salt thereof.

44. A process according to claim 42 in which the 1,L-10-ethyl-10-deazaminopterin is administered in an amount within the range from about 0.1 to about 500 mg per day.

45. A process according to claim 42 in which the 1,L-10-ethyl-10-deazaminopterin is administered with an inert diluent or carrier.

46. A process according to claim 42 in which the 1,L-10-ethyl-10-deazaminopterin is administered orally.

47. A process according to claim 42 in which the 1,L-10-ethyl-10-deazaminopterin is administered parenterally.

* * * * *